United States Patent [19]
Cross, III

[11] Patent Number: 5,718,575
[45] Date of Patent: Feb. 17, 1998

[54] ADJUSTABLE, CUSTOMIZABLE PERFORMANCE ENHANCING DENTAL APPLIANCE

[75] Inventor: Henry D. Cross, III, Murrell's Inlet, S.C.

[73] Assignee: Big Picture, Inc., Minneapolis, Minn.

[21] Appl. No.: 764,900

[22] Filed: Dec. 16, 1996

Related U.S. Application Data

[63] Continuation-in-part of Ser. No. 375,921, Jan. 19, 1995, Pat. No. 5,584,687, which is a continuation of Ser. No. 104,489, Aug. 9, 1993, abandoned.

[51] Int. Cl.$^6$ ..................... A61C 3/00
[52] U.S. Cl. ..................... 433/6; 128/861
[58] Field of Search ................. 433/6; 128/858, 128/859, 860, 861, 862

[56] References Cited

U.S. PATENT DOCUMENTS

| | | |
|---|---|---|
| 257,038 | 4/1882 | McMann . |
| D. 328,494 | 8/1992 | Schwendeman . |
| D. 343,928 | 2/1994 | Kittelsen . |
| D. 356,188 | 3/1995 | Kittelsen . |
| 1,117,928 | 11/1914 | Thurmond . |
| 1,323,832 | 12/1919 | Chige . |
| 1,461,209 | 7/1923 | Bridges . |
| 1,470,888 | 10/1923 | Smedley . |
| 1,487,392 | 3/1924 | Lee . |
| 2,118,980 | 5/1938 | Montgomery et al. . |
| 2,257,709 | 9/1941 | Anderson . |
| 2,630,117 | 3/1953 | Coleman . |
| 2,643,652 | 6/1953 | Cathcart . |
| 2,659,366 | 11/1953 | Savarese . |
| 2,669,988 | 2/1954 | Carpenter . |
| 2,678,043 | 5/1954 | Stark . |
| 2,694,397 | 11/1954 | Herms . |
| 2,702,032 | 2/1955 | Freedland . |
| 2,708,931 | 5/1955 | Freedland . |
| 2,750,941 | 6/1956 | Cathcart . |
| 2,847,003 | 8/1958 | Helmer et al. . |
| 2,966,908 | 1/1961 | Cathcart et al. . |
| 3,016,052 | 1/1962 | Zubren . |
| 3,058,462 | 10/1962 | Greenblum . |
| 3,073,300 | 1/1963 | Berghash . |
| 3,082,765 | 3/1963 | Helmer . |
| 3,107,667 | 10/1963 | Moore . |
| 3,124,129 | 3/1964 | Grossberg . |
| 3,126,002 | 3/1964 | Owens . |
| 3,203,417 | 8/1965 | Helmer . |
| 3,207,153 | 9/1965 | Goldstein . |
| 3,223,085 | 12/1965 | Gores et al. . |
| 3,247,844 | 4/1966 | Berghash . |
| 3,312,218 | 4/1967 | Jacobs . |
| 3,319,626 | 5/1967 | Lindsay . |
| 3,407,809 | 10/1968 | Ross . |

(List continued on next page.)

FOREIGN PATENT DOCUMENTS

| | | |
|---|---|---|
| 1147583 | 6/1983 | Canada . |
| 480423 | 8/1929 | Germany . |

OTHER PUBLICATIONS

*Mouth Protectors: Give Your Teeth a Sporting Chance*, American Dental Association, 1985.

*Muscular Strength Correlated to Jaw Posture and the Temporomandibular Joint*, Stephen D. Smith, D.M.D., NYS Dental Journal, vol. 44, No. 7, Aug.–Sep. 1978.

*Reduction of Stress in the Chewing Mechanism* — Part III, W.B. May, D.D.S., Basal Facts, vol. 3, No. 1, pp. 22–28.

Primary Examiner—Nicholas D. Lucchesi
Attorney, Agent, or Firm—Palmatier, Sjoquist, Helget & Voigt, P.A.

[57] ABSTRACT

A performance enhancing and force absorbing dental appliance for the mouth of an athlete is comprised of an occlusal posterior pad for each side of the posterior teeth engageable with the occlusal surfaces to space apart the teeth, to absorb shock and clenching stress. An arch is provided connecting the posterior pads together within the mouth and out of the way of the tongue to maintain the position of the occlusal posterior pads within the mouth during use and to prevent loss of the pads such as by swallowing.

18 Claims, 4 Drawing Sheets

U.S. PATENT DOCUMENTS

| | | |
|---|---|---|
| 3,411,501 | 11/1968 | Greenberg . |
| 3,448,738 | 6/1969 | Berghash . |
| 3,457,916 | 7/1969 | Wolicki . |
| 3,485,242 | 12/1969 | Greenberg . |
| 3,496,936 | 2/1970 | Gores . |
| 3,505,995 | 4/1970 | Greenberg . |
| 3,513,838 | 5/1970 | Foderick et al. . |
| 3,518,988 | 7/1970 | Gores . |
| 3,532,091 | 10/1970 | Lerman . |
| 3,682,164 | 8/1972 | Miller . |
| 3,692,025 | 9/1972 | Greenberg . |
| 3,768,465 | 10/1973 | Helmer . |
| 3,864,832 | 2/1975 | Carlson . |
| 3,924,638 | 12/1975 | Mann . |
| 3,943,924 | 3/1976 | Kallestad et al. . |
| 4,030,493 | 6/1977 | Walters et al. . |
| 4,044,762 | 8/1977 | Jacobs . |
| 4,063,552 | 12/1977 | Going et al. . |
| 4,114,614 | 9/1978 | Kesling . |
| 4,185,817 | 1/1980 | Peterson . |
| 4,211,008 | 7/1980 | Lerman . |
| 4,330,272 | 5/1982 | Bergersen . |
| 4,337,765 | 7/1982 | Zimmerman . |
| 4,346,205 | 8/1982 | Hiles . |
| 4,348,178 | 9/1982 | Kurz . |
| 4,376,628 | 3/1983 | Aardse . |
| 4,457,708 | 7/1984 | Dufour . |
| 4,519,386 | 5/1985 | Sullivan . |
| 4,568,280 | 2/1986 | Ahlin . |
| 4,591,341 | 5/1986 | Andrews . |
| 4,671,766 | 6/1987 | Norton . |
| 4,672,959 | 6/1987 | May et al. . |
| 4,727,867 | 3/1988 | Knoderer . |
| 4,763,791 | 8/1988 | Halverson et al. . |
| 4,765,324 | 8/1988 | Lake, Jr. . |
| 4,791,941 | 12/1988 | Schaefer . |
| 4,793,803 | 12/1988 | Martz . |
| 4,799,500 | 1/1989 | Newbury . |
| 4,810,192 | 3/1989 | Williams . |
| 4,827,578 | 5/1989 | Heckerman et al. . |
| 4,848,365 | 7/1989 | Guarlotti et al. . |
| 4,867,147 | 9/1989 | Davis . |
| 4,889,533 | 12/1989 | Beecher . |
| 4,924,557 | 5/1990 | Heckerman et al. . |
| 4,977,905 | 12/1990 | Kittelsen et al. . |
| 5,031,638 | 7/1991 | Castaldi . |
| 5,063,940 | 11/1991 | Adell et al. . |
| 5,076,785 | 12/1991 | Tsai . |
| 5,082,007 | 1/1992 | Adell . |
| 5,112,225 | 5/1992 | Diesso . |
| 5,117,816 | 6/1992 | Shapiro et al. . |
| 5,152,301 | 10/1992 | Kittelsen et al. . |
| 5,165,424 | 11/1992 | Silverman . |
| 5,194,004 | 3/1993 | Bergersen . |
| 5,234,005 | 8/1993 | Kittensen et al. . |
| 5,235,991 | 8/1993 | Minneman . |
| 5,259,762 | 11/1993 | Farrell . |
| 5,277,203 | 1/1994 | Hays . |
| 5,293,880 | 3/1994 | Levitt . |
| 5,299,936 | 4/1994 | Ueno . |
| 5,313,960 | 5/1994 | Tomasi . |
| 5,316,474 | 5/1994 | Robertson . |
| 5,320,114 | 6/1994 | Kittelsen et al. . |
| 5,323,787 | 6/1994 | Pratt . |
| 5,336,086 | 8/1994 | Simmen et al. . |
| 5,339,832 | 8/1994 | Kittelsen et al. . |
| 5,353,810 | 10/1994 | Kittelsen et al. . |
| 5,365,946 | 11/1994 | McMillan . |
| 5,385,155 | 1/1995 | Kittelsen et al. . |
| 5,447,168 | 9/1995 | Bancroft . |
| 5,460,527 | 10/1995 | Kittelsen . |
| 5,566,684 | 10/1996 | Wagner . |
| 5,584,687 | 12/1996 | Sullivan et al. . |

ADJUSTABLE, CUSTOMIZABLE PERFORMANCE ENHANCING DENTAL APPLIANCE

This application is a Continuation-in-Part of co-owned patent application Ser. No. 08/375,921, filed on Jan. 19, 1995, now U. S. Pat. No. 5,584,687 which is a continuation of patent application Ser. No. 08/104,489, filed on Aug. 9, 1993, now abandoned, all of which share common inventorship.

BACKGROUND OF THE INVENTION

This invention relates generally to a performance enhancing and force absorbing dental appliance for use by athletes, and more particularly to such an adjustable, customizable appliance that spaces apart the teeth to absorb shock and clenching stress, to space apart the anterior teeth of the lower and upper jaws to facilitate breathing and speech, to lessen condyle pressure, force and impact upon the cartilage and temporomandibular joints, the arteries and the nerves, and to further increase body muscular strength and endurance.

Almost all athletes, such as body builders, weight lifters, baseball batters, golfers, football players, hockey players and bowlers, clench their teeth during exertion which results in hundreds of pounds of compressed force exerted from the lower jaw onto the upper jaw. This clenching force is unevenly transmitted through the jaw structure into the connective tissues and muscles of the lower jaw and further into the neck and back. This can result in headaches, muscle spasms, damage to teeth, injury to the temporomandibular joint, and pain in the jaw. Furthermore, clenching the teeth makes breathing more difficult during physical exercise and endurance when breathing is most important.

There is a need for an adjustable, customizable performance enhancing and force absorbing dental appliance for the mouth of an athlete which will absorb shock and clenching stress otherwise transferred from the connective tissues, the muscles and lower jaw to the upper jaw, neck and back, will space apart the anterior teeth of the lower jaw from the anterior teeth of the upper jaw to facilitate breathing and speech, and will lessen condyle pressure, force and impact upon the cartilage, and temporomandibular joints, arteries and the nerves.

SUMMARY OF THE INVENTION

An adjustable, customizable performance enhancing and force absorbing dental appliance for the mouth of an athlete is comprised of an occlusal posterior pad customizable for each side of the posterior teeth as to be engageable with the occlusal surfaces to space apart the upper and lower teeth, to absorb shock and clenching stress. An adjustable arch with a shape memory is provided connecting the posterior pads together within the mouth and out of the way of the tongue to maintain the position of the occlusal posterior pads within the mouth during use and to prevent loss of the pads such as by swallowing.

A principal object and advantage of the present invention is that the appliance protects the teeth, jaws, gums, connective tissues, back, head and muscles from teeth clenching forces typically exerted during athletic activity.

Another object and advantage of the present invention is that it facilitates breathing and speech during strenuous physical activity such as in power lifting or body building.

Another object and advantage of the present invention is that the appliance places the lower jaw in the power position moving the condyle downwardly and forwardly away from the nerves and arteries within the fossae or socket to increase body muscular strength, greater endurance and improved performance by the appliance user.

Another object and advantage of the present invention is that the appliance is customizable to fit the dentations of the upper and lower posterior teeth and adjustable in the arch to fit the palate structure of the user.

Another object and advantage of the present invention is that the palate's formable and adjustable arch is preferably made of a shape memory alloy of nickel and titanium which will permit the user to refit the appliance should the arch become bent, kinked, twisted or otherwise distorted.

Other objects and advantages will become obvious with the reading of the following specification and appended claims with a review of the Figures.

BRIEF DESCRIPTION OF THE DRAWINGS

FIG. 1B is a perspective view of the appliance arch of shape memory alloy;

DETAILED SPECIFICATION

Figure 1:
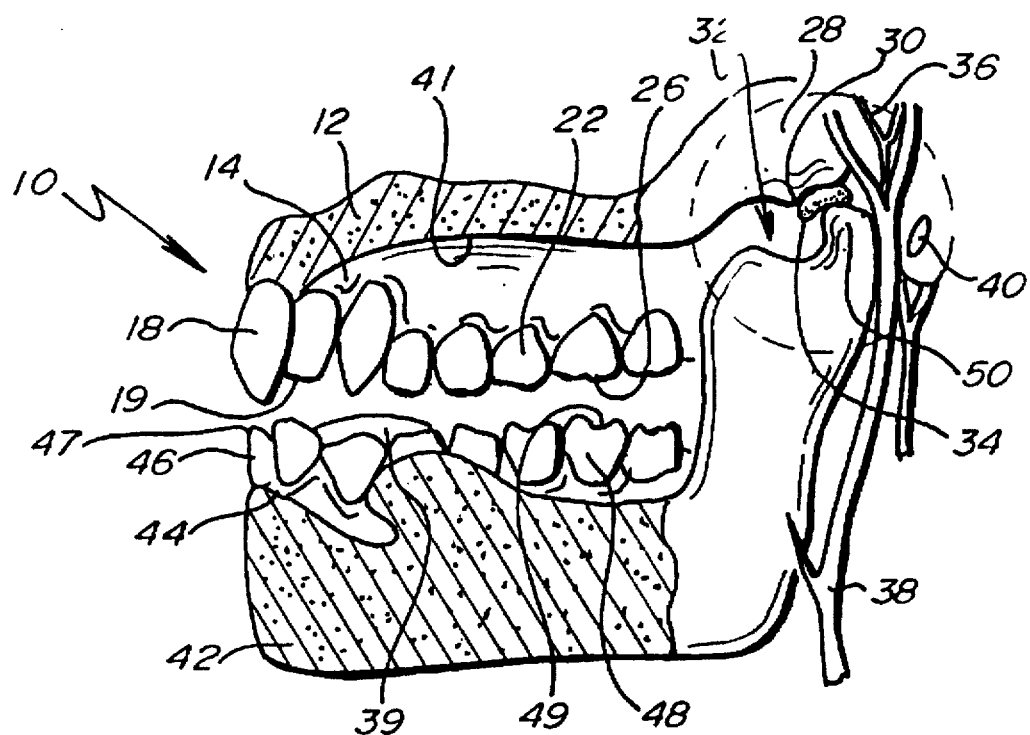
FIG. 1 is a maxillary mandibular buccal or partial side elevational view of the jaws and temporomandibular joint of the user of the dental appliance of the present invention.
Figure 1A:
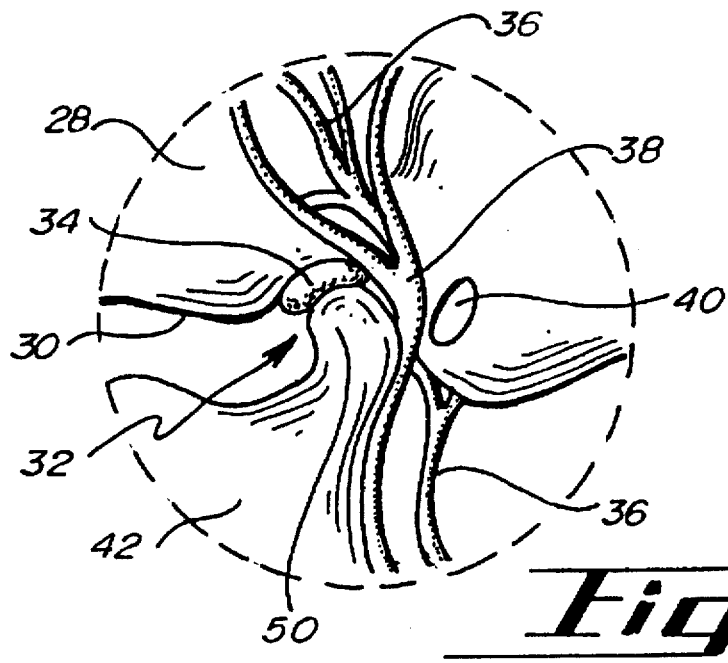
FIG. 1A is an enlarged view of the temporomandibular joint portion of FIG. 1.
Figure 6:
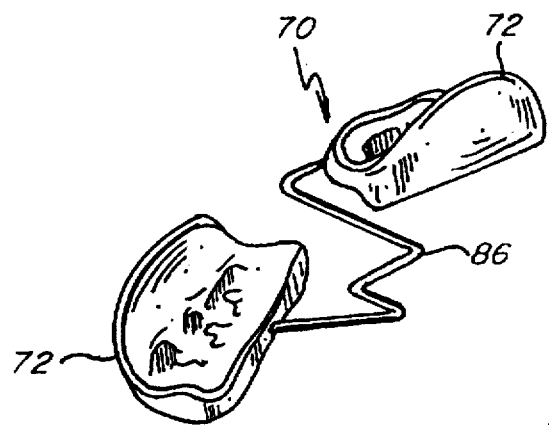
FIG. 6 is a perspective view of the appliance arch bent out of shape.
Figure 7:
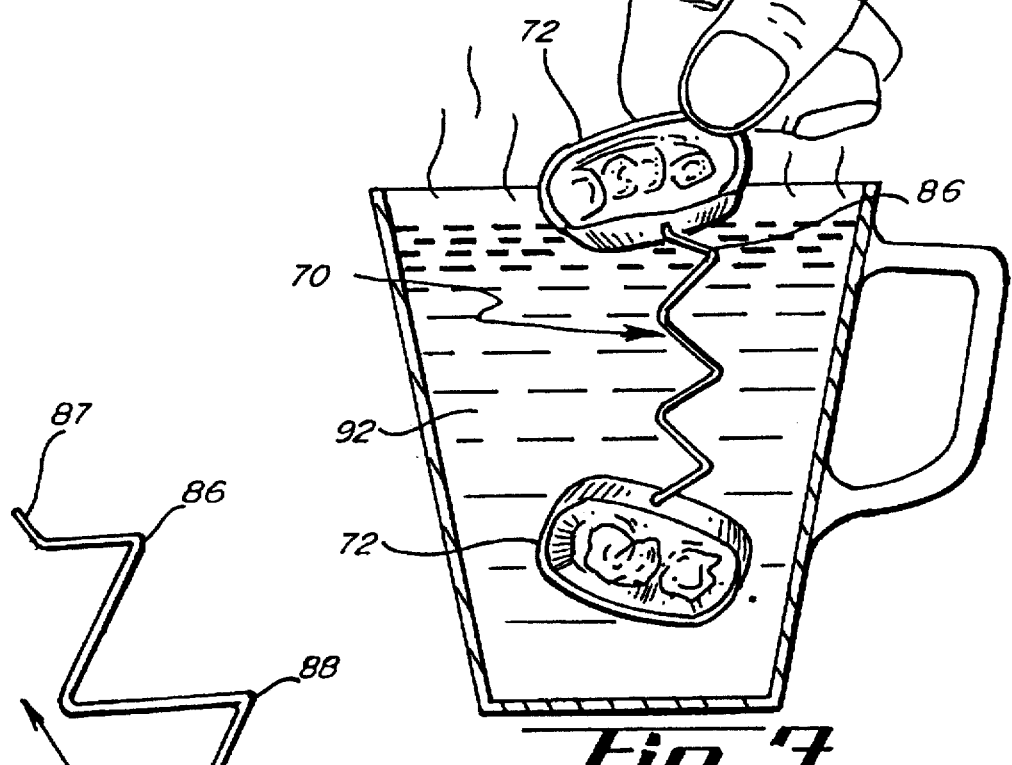
FIG. 7 is an elevational view of the arch being submersed in warm water for straightening.
Figure 18:

To understand the structural features and benefits of the dental appliance 70 of the present invention, some anatomy will first be described. Referring to FIGS. 1 and 1A, the user or athlete has a mouth 10 generally comprised of a rigid upper jaw 12 and a moveable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, supports anterior teeth (incisors and canines) 18 which have incisal or biting surfaces 19. The gum tissues 14 and the bone thereunder also support posterior teeth (molars and bicuspids) 22 which have cusps or biting surfaces 26.

Referring to one side of the human head, the temporal bone 28 is located upwardly and rearwardly of the upper jaw 12 and is in the range of 1/16 to 1/32 inch thick. The articular eminence 30 forms the beginning of the fossa 32 or the socket of the temporomandibular joint 32 and 50. Rearwardly and posteriorly to the articular eminence 30 is located cartilage 34. Through the temporomandibular joint 32 and 50 pass the auriculo-temporalis nerve 36 and the supra-temporo artery 38. Posteriorly to this structure is located the inner ear 40. Within the mouth is located tongue 39 and the roof or hard palate 41 which terminates rearwardly into the soft palate.

The movable jaw or mandible 42 supports a bone covered by gum tissue 44 which further supports anterior teeth (incisors and canines) 46 with incisal or biting surfaces 47 and posterior teeth (molars and bicuspids) 48 with occlusal biting surfaces 49. The condyle 50 of the lower jaw 42 forms the ball of the temporomandibular joint 32 and 50. The anatomical structure is the same for both sides of the head.

Repeated impacts, collisions, blows, stress or forces exerted on the movable lower jaw 42 result in excessive wearing forces upon the condyle 50 and the cartilage or disc 34—typically resulting in deterioration or slippage of the cartilage 34. Thereafter, the lower jaw 42 may be subject to irregular movement, loss of comfortable range of movement and clicking of the joint 32 and 50.

The auriculo-temporalis nerve 36 relates to both sensory and motor activity of the body. Any impingement or pinching of this nerve 36 can result in health problems as previously mentioned. The supra-temporal artery 38 is important in that it provides blood circulation to the head. Impingement, pinching, rupture or blockage of this artery 38 will result in possible loss of consciousness and reduced physical ability and endurance due to the restriction of blood flow to the brain. Thus, it is extremely important to assure that the condyle 50 does not impinge upon the auriculo-temporalis nerve 36 or the supra-temporal artery 38.

It is also important to note that the temporal bone 28 is not too thick. Medical science has known that a sharp shock, stress, or concussive force applied to the lower jaw 42 possibly could result in the condyle 50 protruding through the temporal bone 28, thereby causing death. This incident rarely, but sometimes, occurs with respect to boxing athletes.

Referring to FIGS. 1B through 7, the power enhancing and shock absorbing dental appliance 70 may generally be seen. The appliance 70 has occlusal pads 72 which are suitably made of thermoplastic materials such as copolymers of ethylene and vinyl acetate. It has been found that ethylene vinyl acetate (EVA) is a commercially available compound and approved for oral use by the Food and Drug Administration. The occlusal pads 72 are connected arch 86.

Referring specifically to FIG. 1B, arch 86 in its desired form may be seen. The arch end 87 are molded into occlusal pads 72 when they are formed. The arch is suitably made of a shaped memory alloy suitably of nickel and titanium, preferably in the range of 55 percent nickel and 45 percent titanium. As said, connecting band or wire 86 is preferably made of a titanium base alloy. The stabilizing alloying elements can include manganese, iron, chromium, cobalt, nickel, copper, aluminum, tin and zirconium. Such alloys may also be alpha-titanium or beta-titanium. These alloys exhibit ultra-elasticity and can be made with a memory shape which the wire alloy 86 will return to upon heating. Such a wire product may be obtained from Ultimate Wireforms, Inc., 200 Central Street, Bristol, Conn. 06010. The arch 86 may also be made of stainless steel, annealed wire, braided wire or electrical-like wire.

The arch 86 is in a wire form, which may be 0.02 to 0.05 inches in diameter. 0.032 inches in diameter is found to be optimal. The wire 86 has an undulating or accordion appearance as to permit longitudinal expansion along →A. Thus, the wire has bends 88 along its length. The ends 87 of the arch wire 86 preferably are looped, hooked or form some type of eyelet as to be readily securable when molded into the occlusal pads 72.

The arch wire 86 may have one temperature transition range or multiple temperature transition ranges between the bends 88 and straight portions of the wire 86. For example, the bent 88 end of hooked end portions 87 suitably may have a higher temperature transition range of 110° to 190° while the straight portions between the bends 88 may have a higher temperature transition range of 140° to 220°. Presently, applicant has found the bends 88 suitably should have a temperature transition range of approximately 150° while the straight portions of wire 86 have a temperature transition temperature of 180°. With the lower transition temperature in the bend 88 areas, the shaped memory alloy nickel titanium wire arch 86 is more stiff than the straight portions of the wire 86.

Figure 2:
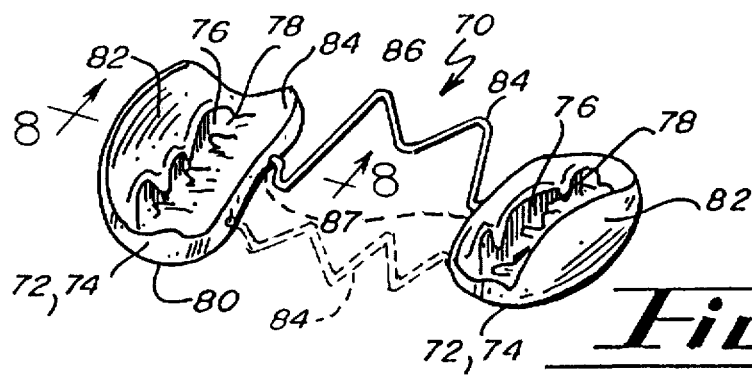
FIG. 2 is a perspective view of the performance enhancing and force absorbing dental appliance.
Figure 3:
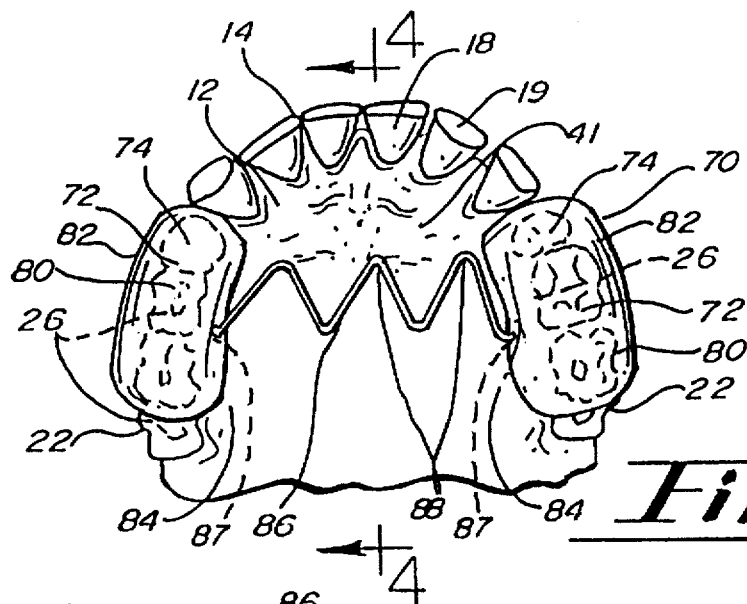
FIG. 3 is a bottom plan view of the upper jaw structure and teeth with the dental appliance in place.
Figure 4:
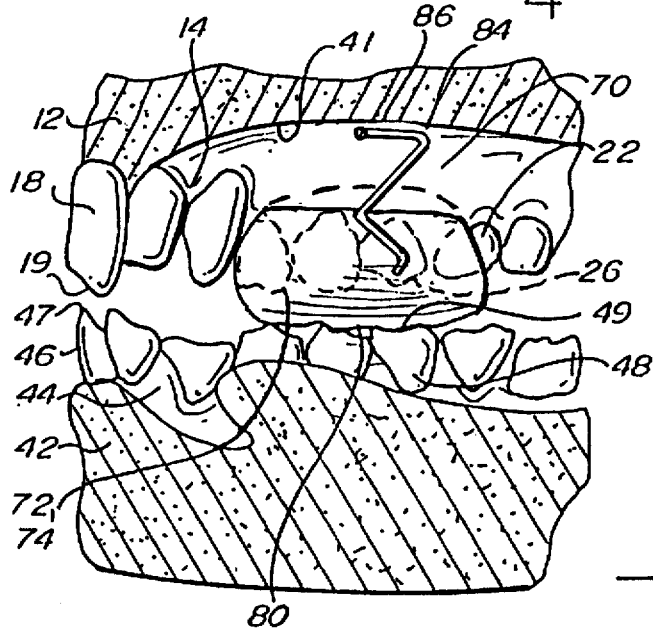
FIG. 4 is a cross-sectional view taken along lines 4—4 of FIG. 3.

Upon the arch structure 86 becoming distorted, it simply may be heated with the boiling water or heat from a match or lighter to spring the arch 86 back into its memorized structure. As can be seen in FIG. 2, the hook or eyelet ends 87 of the arch 86 are molded into the posterior paths 72.

The appliance 70 has posterior occlusal pads 72 each including a base 74 having a fitted top surface 76 with teeth indentations 78 for receiving the posterior teeth 22 of the upper jaw 12 as further explained below. The base 74 has a bottom surface 80 also somewhat conformable to the lower jaw posterior teeth 48. Extending upwardly from base 74 is the labial wall 82 and lingual wall 84.

Figure 5:
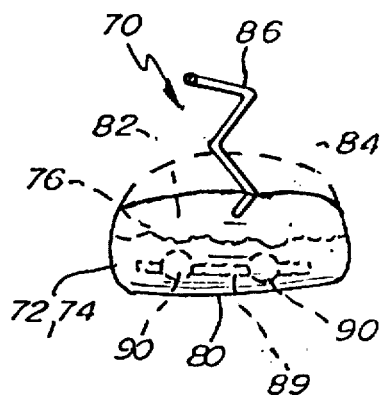
FIG. 5 is a cross-sectional view similar to the appliance in FIG. 4 showing another embodiment.

Optionally, the posterior occlusal pads 72 may have cushions 89 embedded therein appropriately with enlarged portions 90 (FIG. 5). The cushions 89 should suitably be made of a thermoplastic rubber such as that marketed under the trademark Kraton® which is marketed by GLS Plastics of 740B Industrial Drive, Cary, Ill. 60013. This thermoplastic rubber is unique in that it is injection-moldable, FDA approved and readily adheres with copolymers of ethylene and vinyl acetate. Furthermore, the thermoplastic rubber has a melting or softening point significantly higher than that of EVA which will facilitate fitting of the dental appliance 70 to the user or athlete's mouth 10. Furthermore, the thermoplastic rubber, unlike copolymers of ethylene and vinyl acetate, exhibits high resilience, low compression, shape maintenance and shock absorption, attenuation and dissipation. Virtually all rubbers exhibit these physical characteristics which may be utilized for the elastomeric cushion 89.

The enlarged portions 90 of embedded cushion 89 are arranged suitably to be in the bicuspid or molar regions of the teeth 22 and 49. The enlarged portions 90 may take the form of spheres, columns or knobs.

The cushion 89, and optionally the enlarged portions 90, together with the posterior occlusal pads 72 cause the mandible or lower jaw 42 to slide forwardly and slightly downwardly while fitting the dental appliance 70. Also, the condyles 50 are moved downwardly and away from the fossae or sockets 32 without the need for exotic devices and/or measurements, articulation, etc. Furthermore, the posterior cushions 89 and optional enlarged portions 90 assure proper fitting of the appliance 70 when the pads 72 are softened thereby prohibiting the user or athlete from biting too deeply into the soft EVA material of the occlusal pads 72 during fitting.

As is also to be appreciated, the occlusal pads 72 space apart the anterior teeth 18 and 46 while the arch 86 is to be clear of the tongue 39 and the tongue can move freely below the palate 41 which will readily permit the wearer to easily breathe in power fashion as well as convey the ability to speak clearly.

For fitting the appliance 70, the arch 86 may be intermediately bent and grasped thereat and may be momentarily submersed suitably in boiling water for one to two minutes.

Thereafter, the appliance 70 is immediately placed onto the posterior teeth 22 of the upper jaw 12. Next, the lower jaw 42 is positioned forwardly or anteriorly in a range of one to four millimeters as the posterior teeth 48 of the lower movable jaw 42 are positioned on the bottom surface 80 of appliance 70. The wearer or user then applies suction between the upper jaw 12 and the appliance 70 while packing the appliance 70 with the hands along the cheeks adjacent the posterior teeth 22 of the upper jaw 12.

Next, the user may feel along the arch 86 to determine where the arch is not lined along the palate 41. The user takes the appliance 70 out of the mouth and adjusts the lateral length of the arch 86 suitably by stretching or condensing as shown along →A in FIG. 1B. The user next forces the arch 86 upwardly as to permit the arch 86 to properly lie along the palate 86. After this fitting, the appliance 70 is ready for repeated use.

Extending beneath the arch 86 and defined by the arch 86 and the lingual walls 84 of the pads 72 is a tunnel 85. The tunnel 87 is open anteriorly and posteriorly to allow unobstructed movement of the tongue anteriorly and posteriorly.

By this action, the user of the appliance 70 will have correct jaw posture for athletic participation once fitting has been completed and the appliance 70 has cooled. The posterior teeth 48 of the lower jaw 42 will properly index upon the bottom surfaces 80 of the occlusal pads 72. Should the cushions 88 optionally be embedded within the pads 72, they will absorb, attenuate and dissipate shock and stress forces, such as created by clenching. Furthermore, the user will experience increased endurance, performance and muscular freedom due to the power positioning and posture of the TMJ joints 32 and 50.

The user from time to time may not protect the appliance 70 by placement and storage within a container. For instance, the appliance 70 may be placed in a gym bag or golf bag which will permit the arch 86 to become that crushed or otherwise severely distorted shown in FIG. 6. To correct this deformation and to refit the arch 86, the user simply exposes the arch 86 to some heating means, such as hot water 92 shown in FIG. 7. Alternatively, the flame of a lighter or match similarly will permit the shaped memory alloy wire arch 86 to spring back to its original shape for a refitting of the arch 86 along the palate 41.

Figure 8:
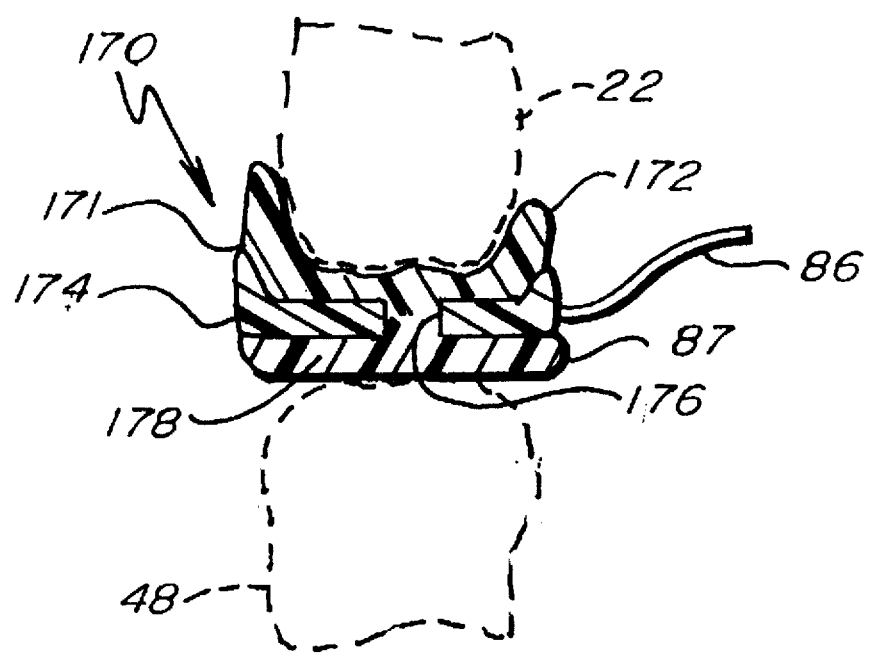
FIG. 8 is a cross of the modified arch taken along lines 8—8 of FIG. 2.

FIG. 8 shows a modified appliance wherein the occlusal pad 171 similar to the occlusal pad 72 of the earlier embodiment is made from a triple composite. The top impressionable layer that is softenable by heat is suitably made of approximately 50% of a polycaprolactone polymer and a 50% composition of 150 ethylene vinyl acetate or EVA. The polycaprolactone polymer is marketed under the name Hydroplastic™ and may be obtained from TAK Systems, P.O. Box 939, East Wareham, Mass. 02538 (disclosed in U.S. Pat. No. 5,112,225). However, the top impressionable layer 172 may be also made solely of EVA.

The intermediate layer is suitably a thermoplastic or thermoplastic rubber such as polyethylene, polypropylene, styrene or the like that is more rigid to securably hold the looped end 87 of the wire or band 86 in place. The intermediate layer 174 has an aperture 176 therethrough to permit an inner locking of the moldable top impressionable layer 172 to the somewhat impressionable bottom or sole layer 178. The bottom or sole layer 178 is suitably made of this thermoplastic elastomer such as a Kraton® and EVA composition. Kraton® is marketed by GLS Plastics of 740B Industrial Drive, Cary, Ill. 60013, and approximately a 50% portion of 150 EVA.

Thus, when the occlusal pad 171 is immersed in hot water, the top layer 172 becomes fairly impressionable while the bottom layer 178 becomes somewhat impressionable to facilitate inter digitation of the upper and lower teeth 22 and 48.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

I claim:

1. A performance enhancing and force absorbing dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through with the auricula-temporalis nerves and supra-temporal arteries pass, the appliance comprising:

(a) a pair of occlusal posterior pads for the posterior teeth on each side of the mouth engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves; and (b) a continuous vertical arch of shape memory alloy wire open anteriorly and posteriorly, extending directly across to and connecting the posterior pads together within the mouth which is shaped as to lie along the palate and out of the way of the tongue to maintain the positions of the occlusal posterior pads within the mouth and to prevent loss of the pads such as by swallowing.

2. The appliance of claim 1, wherein the occlusal posterior pads each have a top surface, a labial wall and a lingual wall conforming to posterior teeth of the upper jaw.

3. The appliance of claim 2, wherein the arch extends from the lingual walls of the occlusal posterior pads.

4. The appliance of claim 1, wherein the arch is an alloy comprised of nickel and titanium.

5. The appliance of claim 1, wherein the posterior pads are made of a low temperature, moldable, thermal plastic.

6. The appliance of claim 5, wherein the thermal plastic is ethylene vinyl acetate.

7. The appliance of claim 5, wherein the pads each have a posterior cushion made of shock absorbing, nonsoftening, resilient, low compression elastomer embedded therein.

8. The appliance of claim 7, wherein the cushions are made of thermoplastic rubber.

9. The appliance of claim 7, wherein the cushions each have enlarged portions.

10. A performance enhancing and force absorbing dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through which the auricula-temporalis nerves and supra-temporal arteries pass, the appliance comprising:

- (a) a pair of thermoplastic occlusal posterior pads for the posterior teeth on each side of the mouth engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves;
- (b) a continuous vertical arch of shape memory alloy wire open anteriorly and posteriorly, adapted to lie along the palate out of the way of the tongue extending directly across to and connecting the posterior pads together within the mouth and out of the way of the tongue to maintain the positions of the occlusal posterior pads within the mouth and to prevent loss of the pads such as by swallowing; and
- (c) a tunnel beneath the arch and defined by the arch and the occlusal posterior pads, the tunnel being completely open anteriorly and posteriorly thereby allowing unobstructed movement of the tongue anteriorly and posteriorly.

11. The appliance of claim 10, wherein the occlusal posterior pads each have a top surface, a labial wall and a lingual wail conforming to posterior teeth of the upper jaw.

12. The appliance of claim 11, wherein the arch extends from the lingual walls of the occlusal posterior pads.

13. The appliance of claim 10, wherein the arch is an alloy comprised of nickel and titanium.

14. The appliance of claim 10, wherein the thermal plastic is ethylene vinyl acetate.

15. The appliance of claim 10, wherein the pads each have a posterior cushion made of a shock absorbing, nonsoftening, resilient, low compression elastomer embedded in the pad.

16. The appliance of claim 15, wherein the cushions are made of thermoplastic rubber.

17. The appliance of claim 16, wherein the cushions each have enlarged portions.

18. A performance enhancing and force absorbing dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through which the auricula-temporalis nerves and supra-temporal arteries pass, the appliance comprising:

- (a) a pair of occlusal posterior pads made of triple composite material with a base having a top surface of impressionable material, and intermediate hard material and a somewhat impressionable bottom layer, the pads being engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves;
- (b) a continuous vertical arch open anteriorly and posteriorly adapted to expose the plate, extending from the intermediate layers of the occlusal posterior pads adapted to lie along the palate out of the way of the tongue extending directly across to and connecting the posterior pads together within the mouth and out of the way of the tongue to maintain the positions of the occlusal posterior pads within the mouth and to prevent loss of the pads such as by swallowing; and
- (c) a tunnel beneath the arch and defined by the arch and the occlusal posterior pads, the tunnel being completely open anteriorly and posteriorly thereby allowing unobstructed movement of the tongue anteriorly and posteriorly.

* * * * *